(12) United States Patent
Hakomori et al.

(10) Patent No.: US 9,247,882 B2
(45) Date of Patent: Feb. 2, 2016

(54) DENTAL APPARATUS, IMAGE ACQUISITION METHOD, AND INFORMATION PROCESSING APPARATUS

(71) Applicant: Sony Corporation, Tokyo (JP)

(72) Inventors: Shiho Hakomori, Kanagawa (JP); Koshi Tamamura, Tokyo (JP)

(73) Assignee: Sony Corporation, Tokyo (JP)

( * ) Notice: Subject to any disclaimer, the term of this patent is extended or adjusted under 35 U.S.C. 154(b) by 142 days.

(21) Appl. No.: 13/902,199

(22) Filed: May 24, 2013

(65) Prior Publication Data

US 2013/0323674 A1 Dec. 5, 2013

(30) Foreign Application Priority Data

Jun. 1, 2012 (JP) .................. 2012-125760

(51) Int. Cl.
 *A61B 5/00* (2006.01)
 *A61B 5/103* (2006.01)
(52) U.S. Cl.
 CPC .............. *A61B 5/0088* (2013.01); *A61B 5/0013* (2013.01); *A61B 5/0071* (2013.01); *A61B 5/742* (2013.01); *A61B 5/1032* (2013.01); *A61B 2576/00* (2013.01)

(58) Field of Classification Search
 CPC ............................ A61C 19/04; A61B 5/0088
 USPC ........................................................... 433/29
 See application file for complete search history.

(56) References Cited

U.S. PATENT DOCUMENTS

| | | | |
|---|---|---|---|
| 7,570,984 B2 * | 8/2009 | Katsuda et al. | 600/407 |
| 7,577,284 B2 * | 8/2009 | Wong et al. | 382/128 |
| 7,668,355 B2 * | 2/2010 | Wong et al. | 382/128 |
| 7,702,139 B2 * | 4/2010 | Liang et al. | 382/128 |
| 8,512,040 B2 * | 8/2013 | Binner et al. | 433/216 |
| 2011/0085713 A1 * | 4/2011 | Yan et al. | 382/128 |
| 2011/0085714 A1 * | 4/2011 | Yan et al. | 382/128 |

FOREIGN PATENT DOCUMENTS

JP 2011-182993 A 9/2011

* cited by examiner

*Primary Examiner* — Ralph Lewis
(74) *Attorney, Agent, or Firm* — Sheridan Ross P.C.

(57) ABSTRACT

A dental apparatus includes a light irradiation unit for emitting a light to irradiate an oral cavity, an image capturing unit for image-capturing the oral cavity light irradiated by the light irradiation unit, and an output unit for outputting data for highlighting and displaying at least one of a plaque site and a calculus site on an image of the oral cavity based on an image captured result by the image capturing unit.

12 Claims, 14 Drawing Sheets

DENTAL APPARATUS, IMAGE ACQUISITION METHOD, AND INFORMATION PROCESSING APPARATUS

BACKGROUND

The present technology relates to a dental apparatus, an image acquisition method, and an information processing apparatus for use in perceiving a status of plaques or calculi by an oral care.

SUMMARY

Daily brushing care is important to prevent periodontitis and caries. A known plaque detection apparatus extracts a tooth flank site and a plaque site based on a color difference in oral cavity image data captured by a camera, and detects the plaque (for example, see Japanese Patent Application Laid-open No. 2011-182993). Japanese Patent Application Laid-open No. 2011-182993 describes a plaque detection apparatus including a picture signal output terminal for displaying a picture that is an image captured by a camera. Using the terminal, a user can see the image displayed, and easily perceive an oral site captured.

In the plaque detection apparatus described in Japanese Patent Application Laid-open No. 2011-182993, the image displayed using the picture signal output terminal is only for perceiving the oral site captured, and the user is incapable of accurately perceiving the plaque site.

It is desirable to provide a dental apparatus and an image acquisition method capable of visually specifying a plaque site and/or a calculus site with clarity.

According to an embodiment of the present technology, there is provided a dental apparatus including a light irradiation unit, an image capturing unit, and an output unit.

The light irradiation unit emits light for irradiating an oral cavity.

The image capturing unit captures an image of the oral cavity with which light is irradiated by the light irradiation unit.

The output unit outputs data for highlighting and displaying at least one of a plaque site and a calculus site on the image of the oral cavity based on an image captured result by the image capturing unit.

According to the present technology, the image of the plaque site or the calculus site is highlighted and displayed, whereby a user can do the oral care by being aware of the plaque site or the calculus site.

The light irradiation unit may emit near-infrared rays, and the output unit may output the data for highlighting and displaying at least one of the plaque site and the calculus site on the image of the oral cavity based on a reflected light amount from the oral cavity emitted to the near-infrared rays irradiated by the light irradiation unit.

In this way, the oral cavity is irradiated with the near-infrared rays, and teeth, calculi, and plaques can be discerned based on the reflected light amount. The plaques contain a higher water content than the teeth and the calculi, and absorb the near-infrared rays, thereby decreasing the reflected light amount. Therefore, it can be discerned that a site where the reflected light amount is high is the teeth or the calculi, and a site where the reflected light amount is low is the plaques.

The output unit may output the data for highlighting and displaying the plaque site and the calculus site being capable of discerning on the image of the oral cavity based on a reflected light amount from the oral cavity emitted to the near-infrared rays irradiated by the light irradiation unit.

In this way, the plaque site and the calculus site may be highlighted and displayed being capable of discerning.

The light irradiation unit may emit p-polarized light, and the output unit may output the data for highlighting and displaying the calculus site on the image of the oral cavity based on an s-polarized light amount of a returned light from the oral cavity emitted to the p-polarized light irradiated by the light irradiation unit.

In this way, the oral cavity is irradiated with the p-polarized light, and the calculi and the teeth can be discerned based on the s-polarized light amount of the returned light from the oral cavity. The calculi have rougher surfaces than the teeth. By evaluating a disturbance of the polarized light due to a surface roughness, the calculi and the teeth can be discerned. When the oral cavity is irradiated with the p-polarized light, a polarized surface is disturbed by the surface roughness of the calculi. Therefore, an intensity of the s-polarized light of the returned light on calculi is greater than that on teeth. Thus, the calculi and the teeth can be discerned.

The irradiation light may be s-polarized light. In this case, a p-polarized light component of the returned light is analyzed to discern the calculi and the teeth. A principle of discernment is similar to that of the irradiation light of the p-polarized light.

The output unit may output the data for highlighting and displaying the calculus site on the image of the oral cavity based on a scattering degree of the reflected light from the oral cavity emitted to the light irradiated by the light irradiation unit.

In this way, the calculi and the teeth can be discerned based on the scattering degree of the reflected light from the oral cavity. The calculi have rougher surfaces than the teeth. By evaluating the scattering degree due to a surface roughness, the calculi and the teeth can be discerned. The light irradiated to the teeth not roughened is less scattered and is reflected and returned. In contrast, the light irradiated to the calculi roughened is scattered and returned. Therefore, in the case where the scattering degree is greater, it can be found that there are the calculi. Thus, the calculi and the teeth can be discerned.

The light irradiation unit may emit a blue light, and the output unit may output the data for highlighting and displaying the plaque site on the image of the oral cavity based on a light amount from the oral cavity emitted to the blue light irradiated by the light irradiation unit.

When the plaques are irradiated with the blue light, they emit fluorescence. Utilizing this, the plaque site can be discerned, and the image where the plaque site is highlighted and displayed can be provided.

A plaque staining agent is administered to the oral cavity, and the output unit may output the data for highlighting and displaying the plaque site on the image of the oral cavity based on a color density stained by the plaque staining agent.

In this way, the plaque site may be discerned based on the color density stained by the plaque staining agent.

The output unit may output the data for visualizing a status change of the plaque site or the calculus site in the oral cavity.

In this way, a removal status at the plaque site or the calculus site can be visually confirmed, for example.

The output unit may output the data for being audible of a status change of the plaque site or the calculus site in the oral cavity.

In this way, a removal status at the plaque site or the calculus site can be audibly confirmed, for example.

According to another embodiment of the present technology, there is provided a dental apparatus including an insertion unit, a gripper unit, a light irradiation unit, and an image capturing unit.

The insertion unit is inserted into the oral cavity.

The gripper unit is connected to the insertion unit.

The light irradiation unit disposed on the insertion unit emits a light for irradiating the oral cavity.

The image capturing unit is disposed on the insertion unit and acquires the image captured result of the oral cavity in order to generate data for highlighting and displaying the plaque site or the calculus site on the image of the oral cavity.

The dental apparatus may further include a cleaning unit for cleaning the oral cavity.

According to still another embodiment of the present technology, there is provided an information processing apparatus including a receiving unit, a control unit, and a display unit.

The receiving unit receives the image captured result of the oral cavity.

The control unit generates an image for highlighting and displaying the plaque site or the calculus site on the image of the oral cavity based on the image captured result.

The display unit displays the image generated.

According to the present technology, the image of the plaque site or the calculus site is highlighted and displayed, whereby a user can do the oral care by being aware of the plaque site or the calculus site.

According to yet another embodiment of the present technology, there is a method of acquiring an image including irradiating an oral cavity with a light, image-capturing the oral cavity, and generating data.

In image-capturing the oral cavity, the oral cavity light irradiated is captured.

In generating data, data is generated in order to highlight and display the plaque site or the calculus site on the image of the oral cavity based on the image captured result.

According to yet another embodiment of the present technology, there is an information processing apparatus including a receiving unit and a control unit.

The receiving unit receives the image captured result of the oral cavity.

The control unit generates an image for highlighting and displaying the plaque site or the calculus site on the image of the oral cavity based on the image captured result.

According to the present technology, the image of the plaque site or the calculus site is highlighted and displayed, whereby a user can do an oral care by being aware of the plaque site or the calculus site.

As described above, according to the present technology, the oral care can be done by visually confirming the plaque site or the calculus site.

These and other objects, features and advantages of the present technology will become more apparent in light of the following detailed description of best mode embodiments thereof, as illustrated in the accompanying drawings.

DETAILED DESCRIPTION OF EMBODIMENTS

Figure 1:
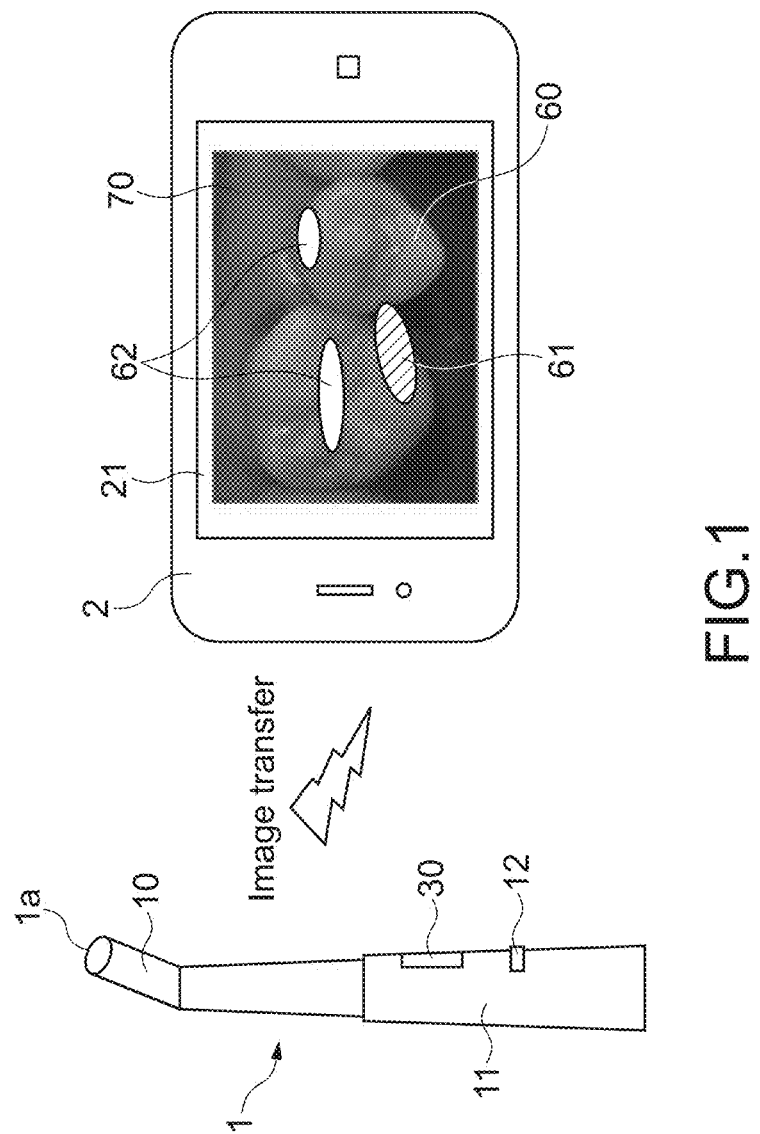
FIG. 1 shows a usage example of a dental apparatus according to a first embodiment of the present technology.

Hereinafter, an embodiment of the present technology will be described with reference to the drawings.

Summary of Embodiments

The embodiments of the present technology relate to a dental apparatus of highlighting and displaying a plaque site and a calculus site to an image of an oral cavity.

In the oral care, perceiving the plaque site is effective for a removal of plaques, and perceiving the calculi encourages a person to visit a dental office, which leads to periodontitis and caries prevention. As an example, when a helper does the oral care of a recipient, the helper perceives the plaque site and the calculus site, whereby a care is certainly done, and an awareness of the helper about the oral care is raised.

The dental apparatus according to an embodiment of the present technology includes a light irradiation unit, an image capturing unit, and the output unit. The light irradiation unit emits light for irradiating an oral cavity. The image capturing unit captures an image of the oral cavity light irradiated by the light irradiation unit. The output unit outputs data for highlighting and displaying at least one of a plaque site and a calculus site on the image of the oral cavity based on the image captured result acquired by the image capturing unit.

Using the dental apparatus according to the embodiment of the present technology, the image of the plaque site or the calculus site is highlighted and displayed, whereby the user can do the oral care by being aware of the plaque site or the calculus site.

As the dental apparatus, the present technology is applicable to a manual toothbrush and an electric toothbrush with a brushing care function, an optical toothbrush having a cleaning function, e.g., a disinfective care function. They may have an image capturing function. Also, the present technology is applicable to a scaler for removing the calculi, and may have the image capturing function. Alternatively, the dental apparatus may only the image capturing function without a care function. The electric toothbrushes include not only an electric toothbrush having a head mechanically vibrated and rotated, but also a sonic toothbrush and a ultrasonic toothbrush that produce a vibration in a sonic or ultrasonic range by a high-speed rotation.

An image processing unit for generating image data for highlighting and displaying the plaque site or the calculus site on the image of the oral cavity based on the image captured result acquired by the image capturing unit may be included in the dental apparatus, or may be included in the information processing apparatus that is connected wired or wireless to the dental apparatus.

The near-infrared rays can be used to discern the plaque site. Based on a reflected light amount from the oral cavity emitted to the near-infrared rays irradiated, the plaque site can be discerned from the teeth and the calculi. The plaques contain a higher water content than the teeth and the calculi, and absorb the near-infrared rays, thereby decreasing the reflected light amount. Therefore, it can be discerned that a site where the reflected light amount is high is the teeth or the calculi, and a site where the reflected light amount is low is the plaques.

P-polarized light can be used for discerning the calculus site. Based on the s-polarized light amount of the returned light from the oral cavity emitted to the p-polarized light irradiated, the teeth and the calculi can be discerned.

The calculi have rougher surfaces than the teeth. By evaluating a disturbance of the polarized light due to a surface roughness, the teeth and the calculi can be discerned. When the oral cavity is irradiated with the p-polarized light, a polarized surface is disturbed by the surface roughness of the calculi. Therefore, an intensity of the s-polarized light of the returned light on calculi is greater than that on teeth. Thus, the calculi and the teeth can be discerned.

The irradiation light s may be s-polarized light. In this case, the p-polarized light component of the returned light is analyzed to discern the calculi from the teeth. A principle of discernment is similar to that of the irradiation light of the p-polarized light.

As another method of discerning the calculus site, based on the scattering degree of the returned light from the oral cavity emitted to the light irradiated by the light irradiation unit, the calculi and the teeth can be discerned. The calculi have rougher surfaces than the teeth. By evaluating the scattering degree due to a surface roughness, the calculi and the teeth can be discerned. The light irradiated to the teeth not roughened is less scattered and is reflected and returned. In contrast, the light irradiated to the calculi roughened is scattered and returned. Therefore, in the case where the scattering degree is greater, it can be found that there are the calculi. Thus, the calculi and the teeth can be discerned.

As another method of discerning the plaque site, the irradiation light of blue light is used. Based on a light amount from the oral cavity emitted to the blue light irradiated, the plaque site can be detected. When the plaques are irradiated with the blue light, they emit fluorescence (autofluorescence). Utilizing this, the plaque site can be discerned.

As still another method of discerning the plaque site, a plaque staining agent may be used. The plaque site can be discerned based on the color density stained by the plaque staining agent. Specifically, the color density is divided into several stages in advance. The site having the color density of a certain stage or more is considered as the plaque site.

When the oral care is done, a status of the plaques may be detected in real time to show a removal status of the plaques as an image or a sound.

Thus, a status change of the plaque site or the calculus site may be visualized or be audibly shown. Herein, "audibly" means that silent data information such as a degree of the plaques attached is outputted as a sound.

Hereinafter, a first embodiment according to the present technology will be described with reference to the drawings.

First Embodiment

A configuration of the dental apparatus according to the first embodiment will be described. In the first embodiment, an optical toothbrush as the dental apparatus has the image capturing function.

[1. Usage Example of Optical Toothbrush]

FIG. 1 shows a usage example of an optical brush 1 as a dental apparatus according to the first embodiment of the present technology.

Figure 2:
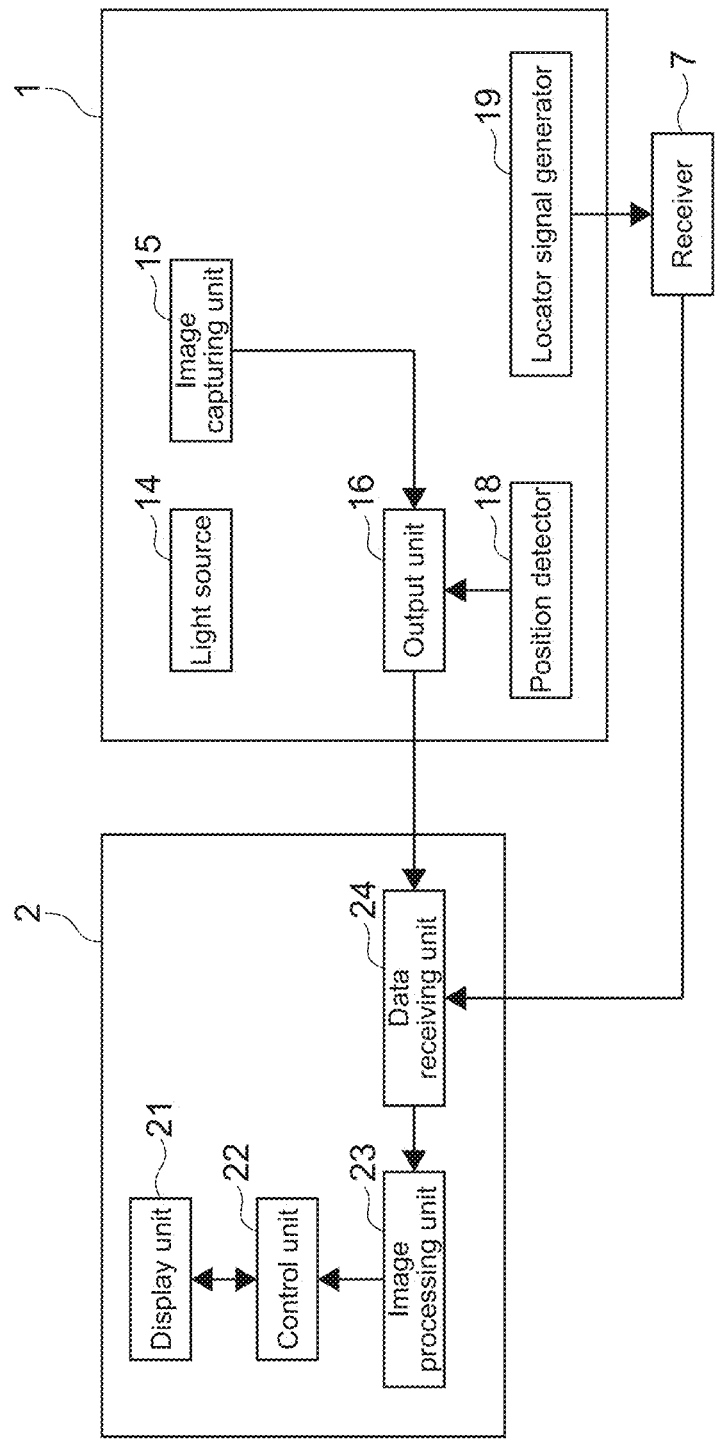
FIG. 2 is a functional block diagram of the dental apparatus shown in FIG. 1.

FIG. 2 is a functional block diagram of the dental apparatus shown in FIG. 1.

As shown in FIG. 1, oral cavity data acquired by the optical toothbrush 1 is transmitted wired or wireless to a smartphone 2 as the information processing apparatus. On a display unit 21 of the smartphone 2, an image of a site where the care is done by the optical toothbrush 1 is displayed. In the image in the oral cavity including a gum 70 and teeth 60 displayed on the display unit 21, calculus sites 62 or a plaque site 61 are/is highlighted and displayed. In the description about the first embodiment below, highlighting and displaying of the plaque site 61 are illustrated as an example.

As shown in FIG. 2, when spatial position information of a probe within the oral cavity is acquired by an image capturing unit included in the optical toothbrush 1, a receiver 7 is disposed to acquire the positional data of an image captured site by the image capturing unit.

[2.1. Configuration of Receiver]

The receiver 7 is in a clip shape being capable of attaching to a nose, an ear and the like, and is used for a spatial position information detector.

The receiver 7 includes a magnetic sensor group in which a number of sensors are arranged.

The receiver 7 is attached by clipping, for example, a right ear lobe when the oral care is done. When the oral care is done using the optical toothbrush 1, the receiver 7 is always attached to the same site.

The receiver 7 forms a reference position when the positional data of the site captured upon capturing an image. The receiver 7 receives a locator signal from a locater signal generation unit 19 as described later, determines the positional data of the site captured as data of an absolute spatial position from the receiver 7 as the reference position, and transmits the data to a data receiving unit 24 of the smartphone 2.

[2.2 Configuration of Optical Toothbrush]

Figure 3:
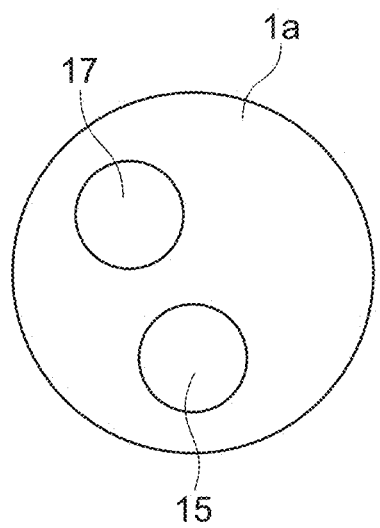
FIG. 3 shows a tip surface of the dental apparatus shown in FIG. 1.

Referring to FIGS. 1 to 3, a configuration of the optical toothbrush will be described.

FIG. 3 shows a tip surface of the optical toothbrush 1.

The optical toothbrush 1 has the care function by the photodisinfection and the image capturing function.

The optical toothbrush 1 emits an excitation light that induces a photodisinfection action. By irradiating the oral cavity to which the sensitizer is administered with the excitation light emitted from the optical toothbrush, periodontitis bacterium that is bonded to the sensitizer administered to the oral cavity is disinfected.

In the care using the optical toothbrush 1, after the user holds a solution or a gel of the sensitizer that absorbs the excitation light in his/her mouth like a mouthwash, the oral cavity is irradiated with the excitation light.

Figure 16:
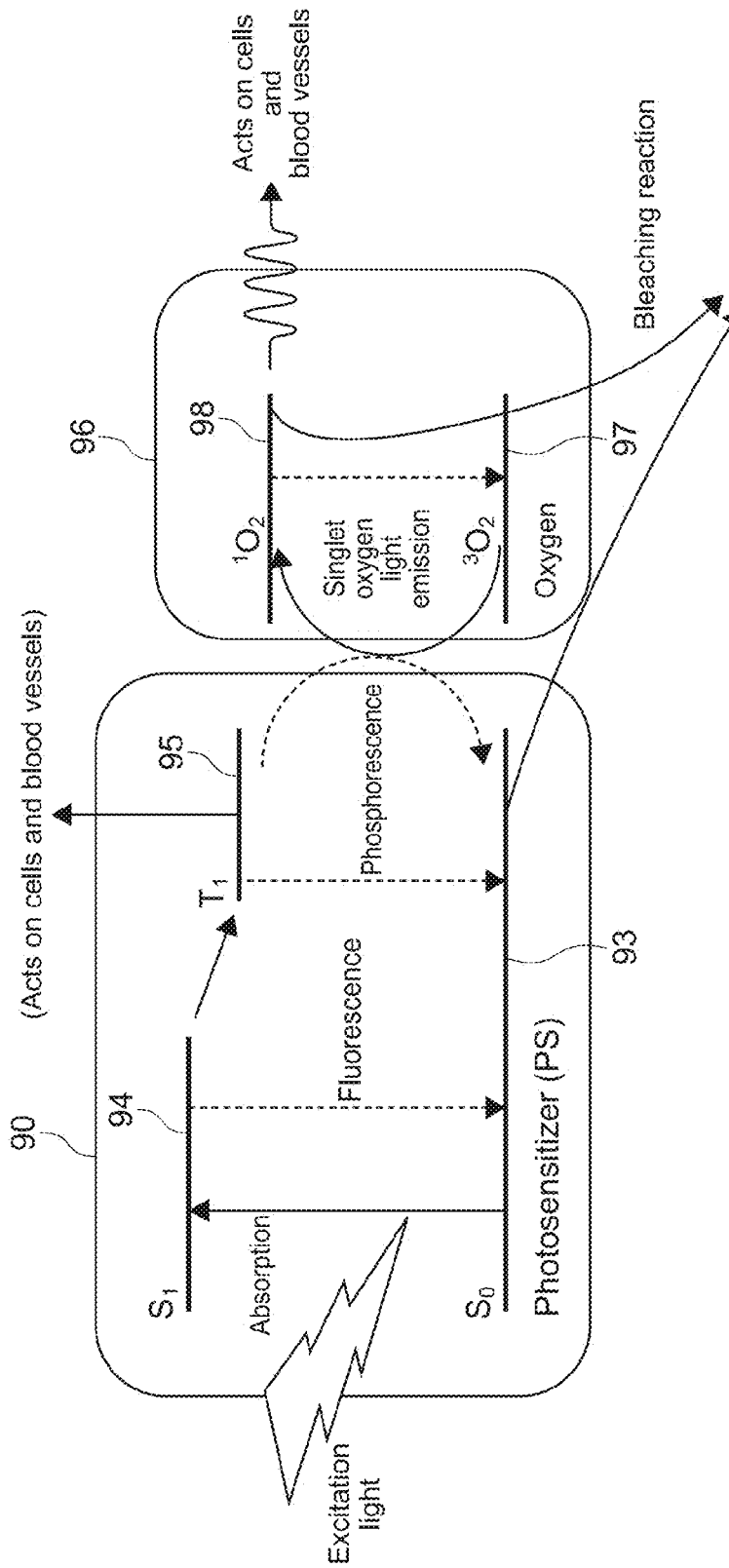
FIG. 16 is a diagram for illustrating a photodisinfection reaction of the dental apparatus according to the first embodiment.

FIG. 16 is a diagram for illustrating the photodisinfection reaction.

A photosensitizer 90 absorbs the excitation light, receives energy and is changed from a ground state 93 to a singlet excited state 94. Most energy is transferred by an intersystem crossing from the singlet excited state 94 to a triplet excited state 95. A part of remaining energy returns from the singlet excited state 94 to the ground state 93. At this point, fluorescence is emitted. In addition, when the photosensitizer 90 in the triplet excited state 95 is collided with oxygen 97 in a triplet state, the energy is transferred to oxygen, and singlet oxygen 98 having high oxidation power is produced. The oxidation power damages surrounding cells and tissues, and destroys (breaches) the photosensitizer 90. By breaching, an amount of the sensitizer to be effective is decreased, and an amount of fluorescence is also decreased. Thus, a decrease in the fluorescence amount forms an indicator of the bleaching and an amount of the tissues damaged.

Here, a surface of the periodontitis bacterium is negatively charged. When a cation photosensitizer such as methylene blue or toluidine blue is administered, the photosensitizer is bonded to the periodontitis bacterium by an electrostatic interaction. Under the state, the excitation light is irradiated to kill only the periodontitis bacterium bonded to the photosensitizer. By administrating a photosensitizer that will be incorporated into the periodontitis bacterium such as indocyanine green (ICG), the periodontitis bacterium in which the photosensitizer is incorporated is killed once the excitation light is irradiated.

In this way, the periodontitis bacterium can be disinfected by the photodisinfection of the optical toothbrush 1.

As the plaques include many periodontitis bacterium, the plaque site can be discerned by the fluorescence emitted by irradiating the excited light. Using the image capturing function of the optical toothbrush 1 according to the first embodiment, the oral cavity is image-captured. By detecting the fluorescence emitted from the oral cavity, the plaque site can be discerned.

As the excitation light of the photosensitizer, a laser light or a light emission diode light can be used.

As shown in FIG. 1, the optical toothbrush 1 includes an insertion unit 10 and a gripper unit 11.

The insertion unit 10 is inserted into the oral cavity when the oral care is done. As shown in FIG. 3, a tip surface 1*a* of the insertion unit 10 includes a light irradiation unit 17 for irradiating laser light emitted from the light source and an image capturing unit 15.

Returning to FIG. 1, the gripper unit 11 is connected to the insertion unit 10. The gripper unit 11 includes a switch 30 for turning on/off the laser light irradiation from the optical toothbrush 1 by the user, and a cleaning notifier 12.

The cleaning notifier 12 lights up, when the tip surface 1*a* becomes dirty, and notifies the user of cleaning. The dirty tip surface a1 affects the image captured result acquired by the image capturing unit 15, and no accurate oral cavity data can be acquired. The dirty tip surface 1*a* is evaluated by the amount of the returned light by the laser light irradiation.

As shown in FIG. 2, the optical toothbrush 1 includes a light source 14, the image capturing unit 15, an output unit 16, a position detector 18 and a locator signal generator 19.

The light source 14 illuminates an image capturing site that is the care site in the oral cavity upon the image capturing, and emits a light for exciting the photosensitizer. Alternatively, another light source may be prepared depending on applications.

The image capturing unit 15 is for image-capturing the oral cavity, and converts the image captured result of the oral cavity on a lens into an electrical signal. As the image capturing unit 15, a CMOS image sensor, a CCD, and an imaging fiber can be used, for example. When the imaging fiber is used, an imaging mechanism and a detector are prepared around a side surface opposite to the insertion unit.

The image-capturing unit 15 spectroscopically detects a received light. In order to increase an SN ratio, a light within a fluorescence wavelength range spectroscopically separated by a dichroic mirror, a diffraction grating or the like is passed through a BPF (band-pass filter) that cuts only a light from a disinfection light source. The image-capturing unit 15 acquires a fluorescence image captured result using a light where the light from the disinfection light source is cut and a fluorescence component is extracted.

An actual image may be captured using another light source for illumination.

The locater signal generation unit 19 transmits the locator signal that is the positional data of the image captured site to the receiver 7, calculates the spatial position information to the receiver 7, and transmits a calculated result to the data receiving unit 24.

The position detector 18 detects an image-capturing angle of the optical toothbrush 1 upon the image capturing.

The output unit 16 outputs the data of the image captured result acquired by the image capturing of the image capturing unit 15 to the data receiving unit 24. Based on the data outputted from the output unit 16, a control unit 22 of the smartphone 2 generates image data for highlighting and displaying the plaque site or the calculus site on the image of the oral cavity.

The output unit 16 transmits image-capturing angle data of the optical toothbrush 1 detected by the position detector 18 and the image captured result acquired by the image capturing unit 15 to the data receiving unit 24.

[2.3. Configuration of Smartphone]

An image processing software for processing the data of the image captured result acquired by the image capturing unit in the optical toothbrush 1 is installed in the smartphone 2 in advance.

As shown in FIG. 1, the smartphone 2 has a display unit 21.

The display unit 21 displays the image of the plaque site 61 or the calculus sites 62, which is/are colored, highlighted and displayed on the image of the oral cavity captured by the image capturing unit 15 included in the optical toothbrush 1. When both of the plaque site 61 and the calculus sites 62 are highlighted and displayed, they are, for example, differently colored so that they are discerned.

As shown in FIG. 2, the smartphone 2 includes the display unit 21, the data receiving unit 24, an image processing unit 23, and the control unit 22.

The data receiving unit 24 receives the data of the image captured result and the data of the image-capturing angle outputted from the output unit 16 in the optical toothbrush 1, and the data of the absolute spatial position transmitted from the receiver 7. The data of the image captured result includes the data of the image captured result for the actual image and the data of the image captured result for fluorescence.

The image processing unit 23 links the data of the image captured result for fluorescence, the data of the absolute spatial position, and the data of the image-capturing angle received by the data receiving unit 24. Hereinafter, the data of the absolute spatial position and the data of the image-capturing angle are referred to as the "positional data" as a whole.

The image processing unit 23 maps gradationally a fluorescence intensity from the data of the image captured result for fluorescence received by the data receiving unit 24, and acquires a fluorescence intensity distribution. The fluorescence intensity is mapped such that the higher the fluorescence intensity detected is, the higher a colored density is. As the plaques may exist on the site where the fluorescence is detected, it is considered that the higher the gradationally mapped density is, the higher the amount of the plaques is.

The control unit 22 correlates the data of the image captured result for the actual image to which the positional data is linked with the data of the image captured result for fluorescence to which the positional data is linked, and generates the image data for highlighting and displaying the plaque site on the image of the oral cavity. The control unit 22 controls the display on the display unit 21, and displays the highlighted and displayed image of the plaque site 61 colored on the image of the oral cavity.

Figure 5:
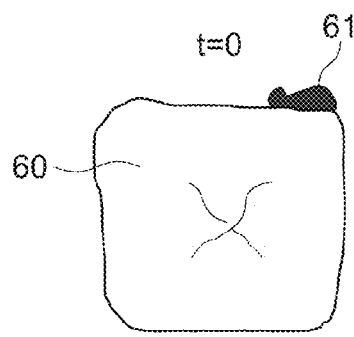
FIG. 5 shows an image acquired by the flow shown in FIG. 4 when time t=0.
Figure 6:
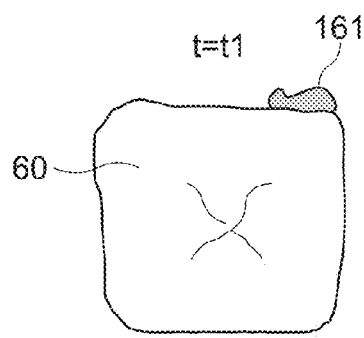
FIG. 6 shows an image acquired by the flow shown in FIG. 4 when time t=t1.
Figure 7:
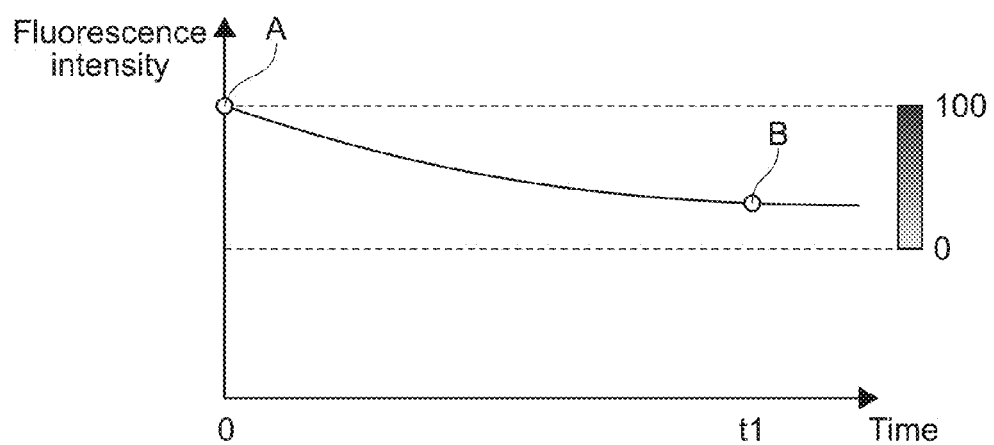
FIG. 7 is a graph showing a disinfective effect by the dental apparatus shown in FIG. 1.

Further, the control unit 22 generates the image data for displaying the temporal change in the status of the plaque site 61 by the oral care based on the data of the fluorescence amount by a temporal change, and displays the image for displaying the temporal change in the status of the plaque site 61 on the display unit 21 as shown in FIGS. 5 and 6 or 7. In other words, the control unit 22 generates the data for visualizing the status change of the plaque site or the calculus site.

FIG. 5 shows a status of the plaque 61 attached to the tooth 60 when the oral care is started at a time t=0. FIG. 6 shows a status of the plaque 161 attached to the tooth 60 after time t1 is past from the start of the oral care. FIG. 7 shows the temporal change in the status of the fluorescence intensity in the oral care, i.e., the removal status of the plaques.

As an example, the temporal change in the status of the plaque site 61 in the oral care can be gradationally shown as an amount of the plaques as shown in FIGS. 5 and 6, so that the higher the amount of the plaque is, the greater a color density of the plaque site 61 is, and the lower the amount of the plaque is, the lower the color density of the plaque site 161 is.

Also, as an example, the temporal change in the status of the plaque site 61 in the oral care can be as a graph for plotting the temporal change of the fluorescence intensity at one plaque site, as shown in FIG. 7. In FIG. 7, a point A corresponds to a plot of the fluorescence intensity at the plaque site 61 at the time t=0 as shown in FIG. 5, and a point B corresponds to a plot of the fluorescence intensity at the plaque site 161 at the time t=t1 as shown in FIG. 6.

A gradation bar at a right side of the graph shown in FIG. 7 represents the color density of the colored plaque site 61. The fluorescence intensity is taken as 100 when t=0. When the fluorescence intensity is 100, the color density is a maximum to be displayed in color. In the gradation bar at the right side of the graph shown in FIG. 7, no color is displayed when the fluorescence intensity is 0, i.e., the plaques are removed.

The information processing apparatus having the display unit is not limited to the smartphone that is a PDA (Personal Digital Assistant) according to the first embodiment, and may have a dedicated display.

According to the first embodiment, the care status such as the plaque removal status is displayed as the image, but may be shown as a sound. For example, when the fluorescence intensity becomes about 80% of that upon the start of the care, a first alert sound, e.g., "pi, pi . . . " is rung. When the fluorescence intensity becomes the same for a predetermined time, a second alert sound, e.g., "pii, pii, pii . . . " is rung, which may inform that the care is ended. Thus, the care status may be visualized on the display and also may be audibly shown. Alternatively, the care status may only be audibly shown without displaying the image. Accordingly, even if the information processing apparatus having the display unit such as the smartphone and the dedicated display cannot be used, the care status can be perceived.

When the care status is shown by the sound, the control unit 22 generates audible data of the status change of the plaques (the removal status).

Also, the removal status of the plaques may be shown as a numerical value. In this case, the removal of the plaques can be perceived by a decreased numerical value.

[Image Acquisition Method]

Next, the method of acquiring the image for highlighting and displaying the plaques will be described using the above-described optical toothbrush 1.

Figure 4:
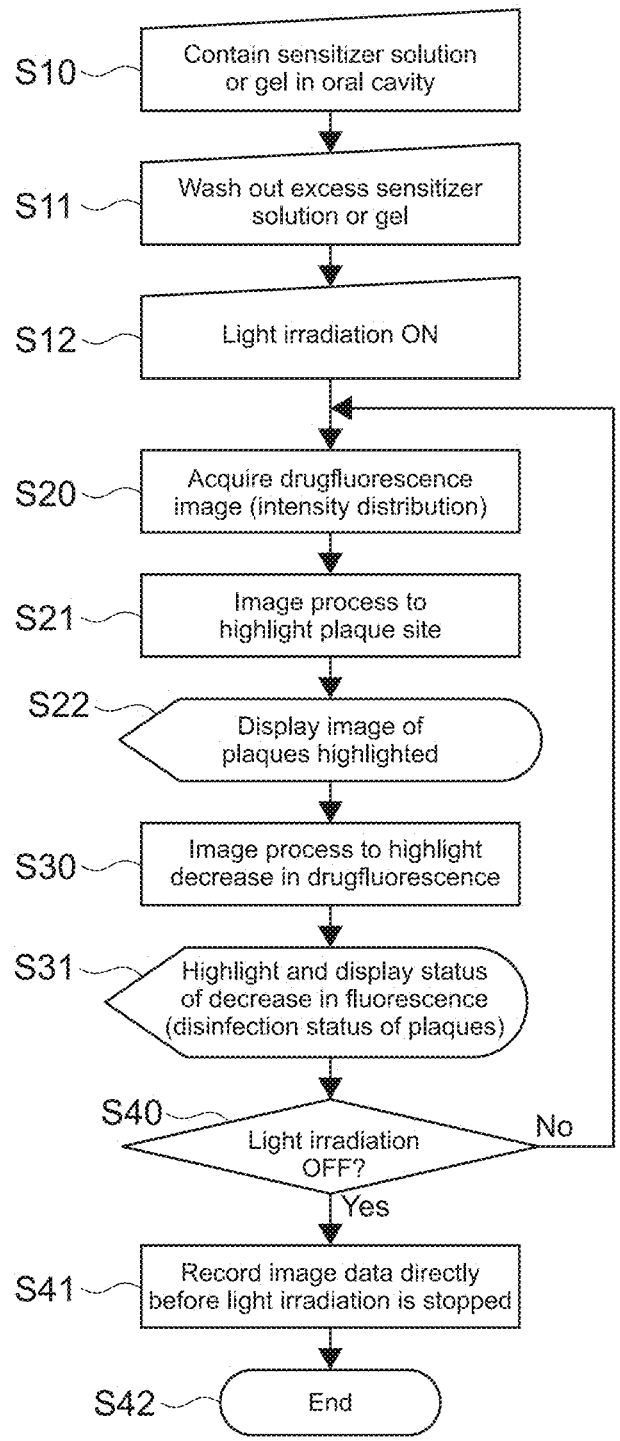
FIG. 4 is a flow diagram showing a flow of image acquisition using the dental apparatus shown in FIG. 1.

FIG. 4 is a flow diagram for acquiring the image for highlighting and displaying the plaques according to the first embodiment. Hereinafter, it will be described along the flow shown in FIG. 4.

(Image Acquisition Preparation Processing, an S10 Number)

After the solution or the gel of the sensitizer is administered to the oral cavity (S10), the excess solution or the gel of the sensitizer is washed out (S11).

By inserting the insertion unit 10 of the optical toothbrush 1 into the oral cavity, and turning on the switch 30 for controlling emission of the light from the optical toothbrush 1 by the user (S12), a laser light is emitted from the light irradiation unit 17 of the optical toothbrush 1.

(Image Acquisition Processing of Plaque Site Highlighted and Displayed, an S20 Number)

The image capturing unit 15 of the optical toothbrush 1 captures an image of the oral cavity to which the light is irradiated from the light irradiation unit 17, and acquires the data of the image captured result for the actual image and the data of the image captured result for fluorescence (an intensity distribution of the drugfluorescence image) (S20). The output unit 16 outputs the data of the image captured result to the image processing unit 23.

The image processing unit 23 maps gradationally the fluorescence intensity from the data of the image captured result for fluorescence received by the data receiving unit 24, and does the image processing for highlighting the plaque site (S21).

Although not in the flow diagram, the position detector 18 detects the image-capturing angle of the optical toothbrush 1 upon the image capturing, and the output unit 16 outputs the image-capturing angle of the optical toothbrush 1 detected by the position detector 18 to the data receiving unit 24. In addition, the receiver 7 receives the locator signal from the locater signal generation unit 19, determines the absolute spatial position of the site captured, and transmits it to the data receiving unit 24. The image processing unit 23 links the data of the image captured result for the actual image with the positional data, and the data of the image captured result for fluorescence with the positional data.

The control unit 22 correlates the data of the image captured result for the actual image to which the positional data is linked with the data of the image captured result for fluorescence to which the positional data is linked, and generates the image data for highlighting and displaying the plaque site on the image of the oral cavity. The control unit 22 displays the highlighted and displayed data of the plaque site 61 on the image of the oral cavity (S22).

(Image Acquisition Processing Showing Temporal Change in Fluorescence Intensity, an S 30 Number)

The image processing unit 23 generates the data of the temporal change in the fluorescence intensity from the data of the image captured result for fluorescence. Further, the image processing unit 23 does the image processing for highlighting and displaying the status of the plaques attached to the tooth 60 at a color density based on the temporal change in the status of the fluorescence intensity, as shown in FIGS. 5 and 6 (S30).

The control unit 22 displays the image highlighted and displayed a status of decreasing the plaques by the care (a disinfection status of the plaques) on the display unit 21 based on the image processing for highlighting and displaying the plaques acquired at S30 (S31). Specifically, as shown in FIGS. 5 and 6, the color of the plaque site 16 is changed and displayed, whereby the disinfection status is displayed. In this case, by displaying the image upon the start of the care as shown in FIG. 5 next to the image after time t1 past from the start of the oral care as shown in FIG. 6, the disinfection status can be perceived based on a colored degree of the plaque site 61.

In order to highlight and display the disinfection status of the plaques, the graph for plotting the temporal change of the fluorescence intensity may be displayed, as shown in FIG. 7, thereby perceiving the disinfection status. Also, FIGS. 5 to 7 may be displayed on one screen.

(End Processing, an S40 Number)

Next, it is determined whether or not the light irradiation by a practitioner is turned off (S40).

At S40, when the control unit determines that the light irradiation is turned off (Yes), the control unit 22 records the image data directly before the laser light irradiation is stopped to a recording unit (not shown) (S41), and ends the care (S42).

When the control unit determines that the light irradiation is not turned off at S40 (No), the flow is returned to S20, and the processing is repeated.

Figure 17:
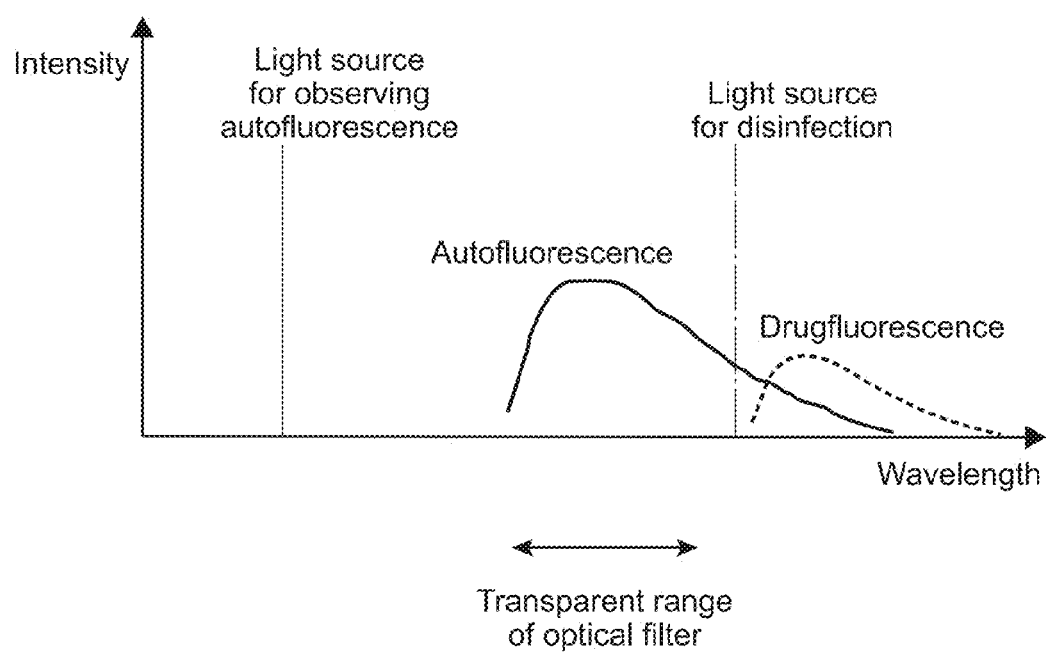
FIG. 17 is a graph showing a relationship between wavelengths of respective light sources and wavelength characteristics of autofluorescence and drugfluorescence.

Here, by irradiating the excitation light that induces the photodisinfection, the plaque site is discerned by fluorescence emitted from the oral cavity. However, autofluorescence may be used to discern the plaque site. When the plaque site is discerned using autofluorescence, a light source of blue light for observing autofluorescence and a light source for disinfection (a light source for the excitation light) may be disposed as two irradiation light sources. The light source of blue light may also be used as the light source for disinfection, but a light source of red light may be useful due to its light reachability. As shown in FIG. 17, the light source for observing autofluorescence and the light source for disinfection may have different wavelengths. As the plaques emit light (autofluorescence) by irradiating the blue light, the disinfection status can be perceived by an intensity of the autofluorescence. Also, as shown in FIG. 17, the wavelength of the autofluorescence and the wavelength of the drugfluorescence are different. When the plaque site is discerned using the autofluorescence, a filter that can cut the drugfluorescence may be used.

As described above, by disposing the image capturing unit 15 on the optical toothbrush 1 and acquiring the image for highlighting and displaying the plaque site based on the image captured result by the image capturing unit 15, the user can perceive the plaque site, and the oral care can be done effectively.

Also, the temporal change in the status of the plaque site in the oral care can be observed, whereby the removal status of the plaques in the oral care can be perceived in real time.

Next, a second embodiment will be described.

Second Embodiment

In the first embodiment, as the dental apparatus, the optical toothbrush has been illustrated. In the second embodiment, as the dental apparatus, an electric toothbrush will be illustrated.

In the first embodiment, the photosensitizer has been used and the plaque site is highlighted and displayed based on the fluorescence emitted from the photosensitizer. In contrast, in the second embodiment, without using the photosensitizer, near-infrared rays are used as the irradiation light to discern the plaques, the calculi and the teeth. In addition, using the p-polarized light as the irradiation light, the calculi and the teeth are discerned. Using discerned results, the plaque site and the calculus site are highlighted and displayed being capable of discerning.

The second embodiment will be described using the drawings below. The similar configurations as the first embodiment are denoted by the same reference numerals, and thus detailed description thereof will be omitted.

According to the second embodiment, an electric toothbrush having a cleaning function is provided with an image-capturing function.

[1. Usage Example of Electric Toothbrush]

Figure 8:
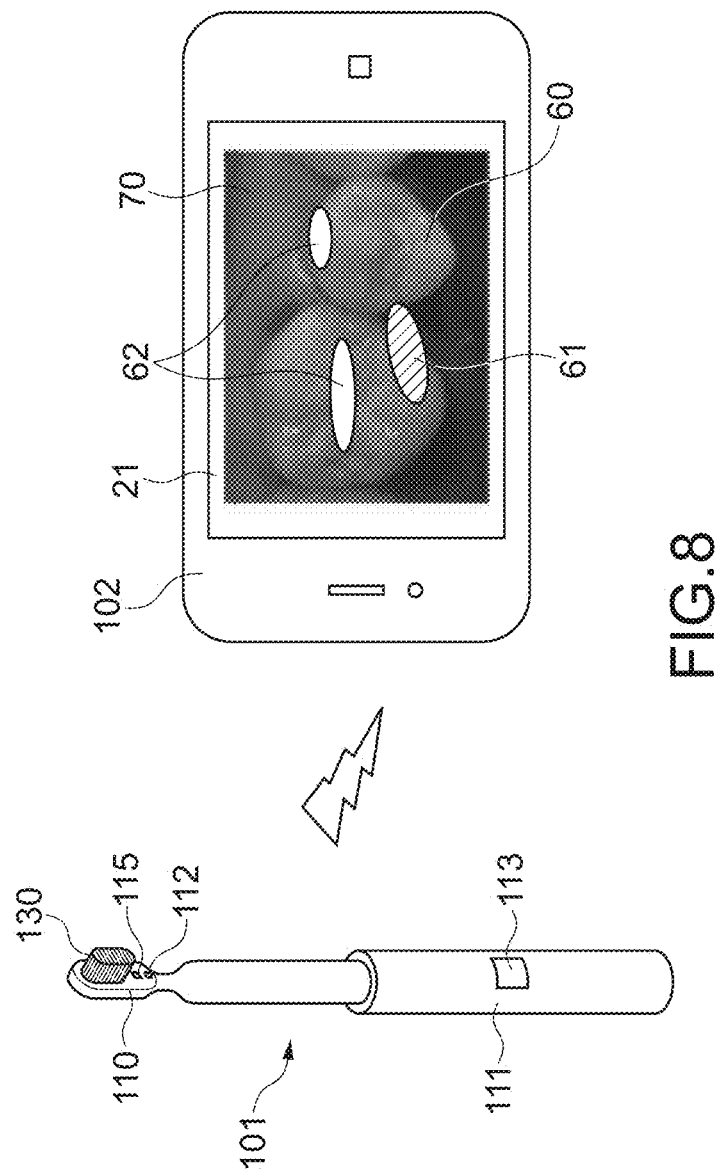
FIG. 8 shows a usage example of a dental apparatus according to a second embodiment of the present technology.

FIG. 8 shows a usage example of an electric toothbrush 101 as the dental apparatus according to the second embodiment.

Figure 9:
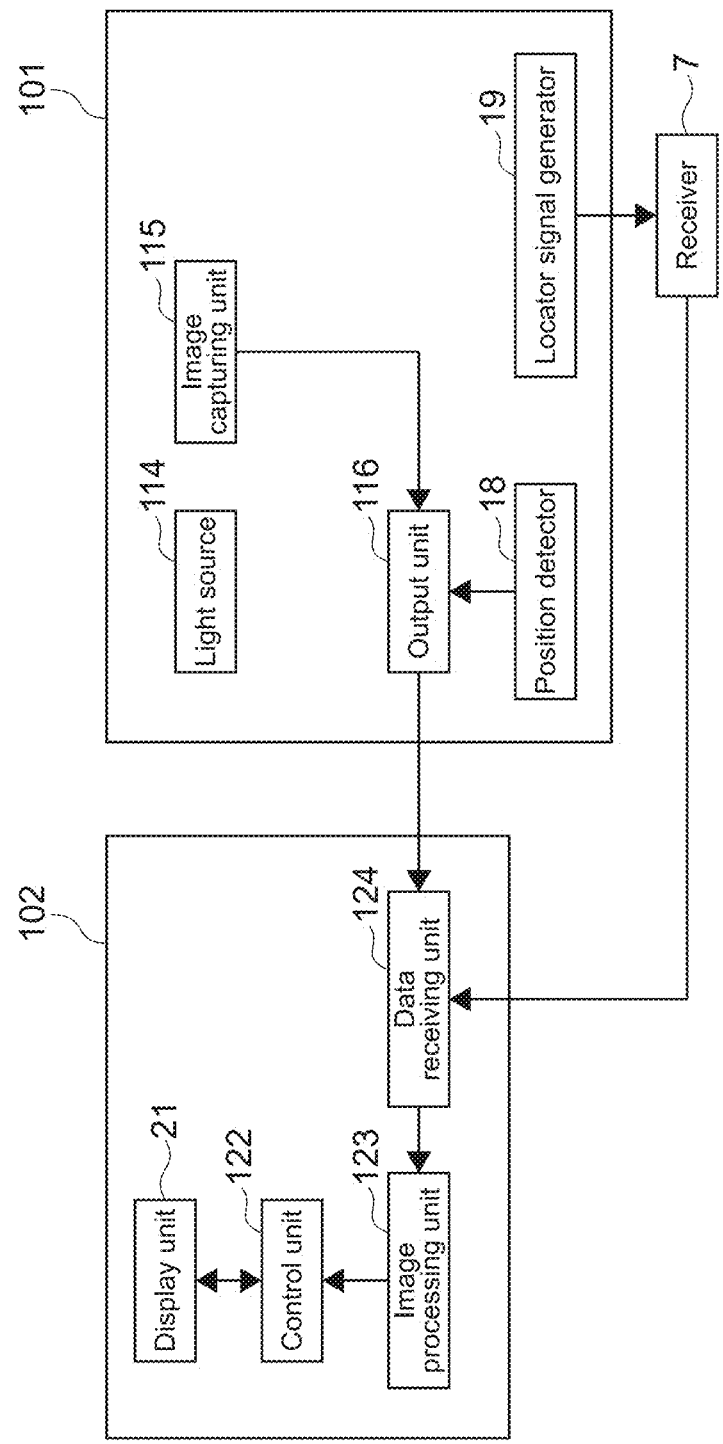
FIG. 9 is a functional block diagram of the dental apparatus shown in FIG. 8.

FIG. 9 is a functional block diagram of the electric toothbrush 101 shown in FIG. 8.

As shown in FIG. 8, the image captured result of the oral cavity acquired by the electric toothbrush 101 is transmitted wired or wireless to a smartphone 102 as the information processing apparatus. On a display unit 21 of the smartphone 102, an image of a site where the care is done by the electric toothbrush 101 is displayed. In the image in the oral cavity including a gum 70 and teeth 60 displayed on the display unit 21, calculus sites 62 or a plaque site 61 are/is highlighted and displayed.

As shown in FIG. 9, when the data in the oral cavity is acquired by an image-capturing unit of the electric toothbrush 101, the receive 7 is disposed to acquire the positional data of an image captured site by the image capturing unit.

[2.1. Configuration of Electric Toothbrush]

As shown in FIG. 8, the electric toothbrush 101 includes an insertion unit 101 and a gripper unit 111.

An insertion unit 110 is inserted into the oral cavity when the care is done. At a tip of the insertion unit 110, a brush 130 for cleaning is disposed. Immediately below of the brush 130, an image capturing unit 115 and a light irradiation unit 112 for irradiating a light emitted from a light source are disposed in this order.

The gripper unit 111 is connected to the insertion unit 110. The gripper unit 111 includes a switch 113 for turning on/off the light irradiation from the optical toothbrush by the user.

As shown in FIG. 9, the electric toothbrush 101 includes a light source 114, the image capturing unit 115, an output unit 116, and the locater signal generation unit 19.

The light source 114 include an image capturing light source for acquiring an actual image, a near-infrared ray light source for detecting a water content, and a p-polarized light source, each of which irradiates a light and stops the irradiation of the light pursuant to an off/off demand by the user. The near-infrared rays emitted from the light source 114 are irradiated to the care site in order to discern the plaques, the calculi and the teeth. The p-polarized light emitted from the light source 114 is irradiated to the care site in order to discern the plaques, the calculi and the teeth.

The image capturing unit 115 converts the image captured result of the oral cavity on a lens into an electrical signal. As the image capturing unit 115, the CMOS image sensor and the CCD can be used, for example.

The image captured result for the actual image acquired by the image capturing unit 115 is transmitted to a data receiving unit 124 of the smartphone 2 by the output unit, as described later.

The output unit 116 outputs the data of the image captured result acquired by image-capturing of the image capturing unit 115 to the data receiving unit 124. Based on the data outputted from the output unit 116, the image data for highlighting and displaying the plaque site or the calculus site on the image of the oral cavity is generated at a control unit 122 of the smartphone 102.

The output unit 116 transmits image-capturing angle data of the electric toothbrush 101 detected by the position detector 18 and the image captured result acquired by the image capturing unit 115 to the data receiving unit 124.

[2.2. Configuration of Smartphone]

An image processing software for processing the data of the image captured result acquired by the image capturing unit 115 in the electric toothbrush 101 is installed in the smartphone 102 in advance.

As shown in FIG. 9, the smartphone 102 has the display unit 21, the control unit 122, the data receiving unit 124, and an image processing unit 123.

The display unit 21 displays the image of the plaque site 61 and the calculus sites 62, which are colored, highlighted and displayed on the image of the oral cavity captured by the image capturing unit 115 in the electric toothbrush 101.

The data receiving unit 124 receives the data of the image captured result and the data of the image-capturing angle outputted from the output unit 116 in the electric toothbrush 101, and the data of the absolute spatial position transmitted from the receiver 7.

The image processing unit 123 maps gradationally a reflected light intensity from the data of the image captured result for the actual image received by the data receiving unit 124, and acquires a reflected light intensity distribution.

The image processing unit 123 links the reflected light intensity distribution with the positional data.

The image processing unit 123 links the data of the image captured result for the actual image received by the data receiving unit 124 with the positional data.

In the second embodiment, the teeth and the calculi are discerned from the plaques by the intensity distribution of the reflected light emitted to the near-infrared rays irradiated by the light irradiation unit 112. In addition, the teeth and the calculi are discerned by an s-polarized light intensity of a returned light from the oral cavity emitted to the p-polarized light irradiated by the light irradiation unit 112.

Figure 11:
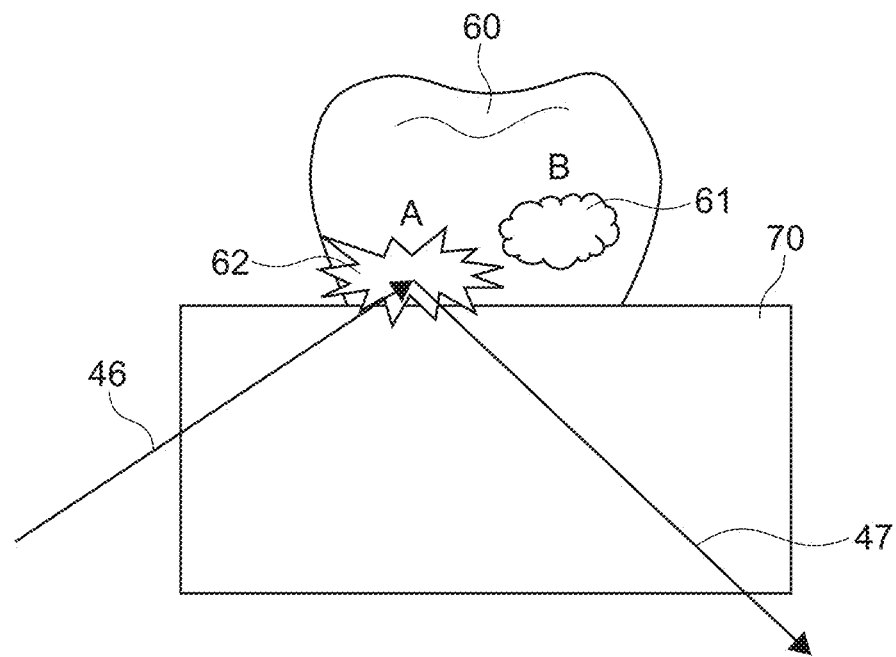
FIG. 11 is a diagram for illustrating a method of discerning a plaque from a calculus by a difference in a water content.

FIG. 11 illustrates that the oral cavity including the tooth 60 and the gum 70 are irradiated with the infrared light.

Figure 12:
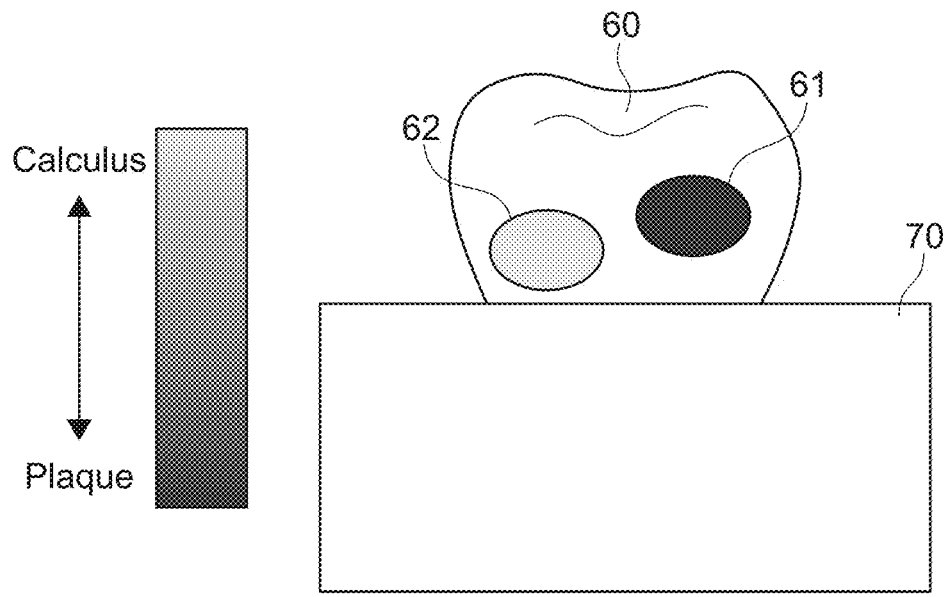
FIG. 12 shows an image example for discerning the plaque site from the calculus site acquired by the method shown in FIG. 11.

FIG. 12 shows an example that the plaque site 61 and the calculus site 62 are highlighted and displayed. The teeth, the calculi and the plaques are discerned based on the reflected light amount to the irradiation of the near-infrared light, and the s-polarized light intensity of the returned light by the p-polarized light irradiation. In FIG. 12, a detected light amount is gradationally shown. In addition, the plaque site and the calculus site may be displayed in different colors.

The water content of the plaques is about 80%, and the water content of the teeth is about 4%. Since the plaques are calcified to the calculi, the water content of the calculi is low. The plaques have a higher water content than the calculi and the teeth, and absorb the near-infrared light. When the oral cavity is irradiated with the near-infrared light, the reflected light amount of the plaques is lower than those of the teeth and the calculi. Thus, by irradiating the near-infrared light, it can be discerned the teeth, the calculi, and the plaques based on the reflected light amount, such that the higher reflected light amount represents the teeth and the calculi and the lower reflected light amount represents the plaques.

In addition, the teeth and the calculi may be discerned by the difference in the reflected light amount to the infra-red light irradiation based on the difference in the water content of the teeth and the calculi.

Furthermore, the p-polarized light can be used to discern the teeth with the calculi. Based on the s-polarized light amount of the returned light from the oral cavity emitted to the p-polarized light irradiated, the teeth and the calculi can be discerned. The plaques have rougher surfaces than the teeth. By evaluating a disturbance of the polarized light due to a surface roughness, the calculi and the teeth can be discerned. When the oral cavity is irradiated with the p-polarized light, the polarized surface is disturbed by the surface roughness of the calculi. Therefore, the intensity of the s-polarized light of the returned light on the calculi is greater than that on the teeth. Thus, the calculi and the teeth can be discerned.

Figure 13:
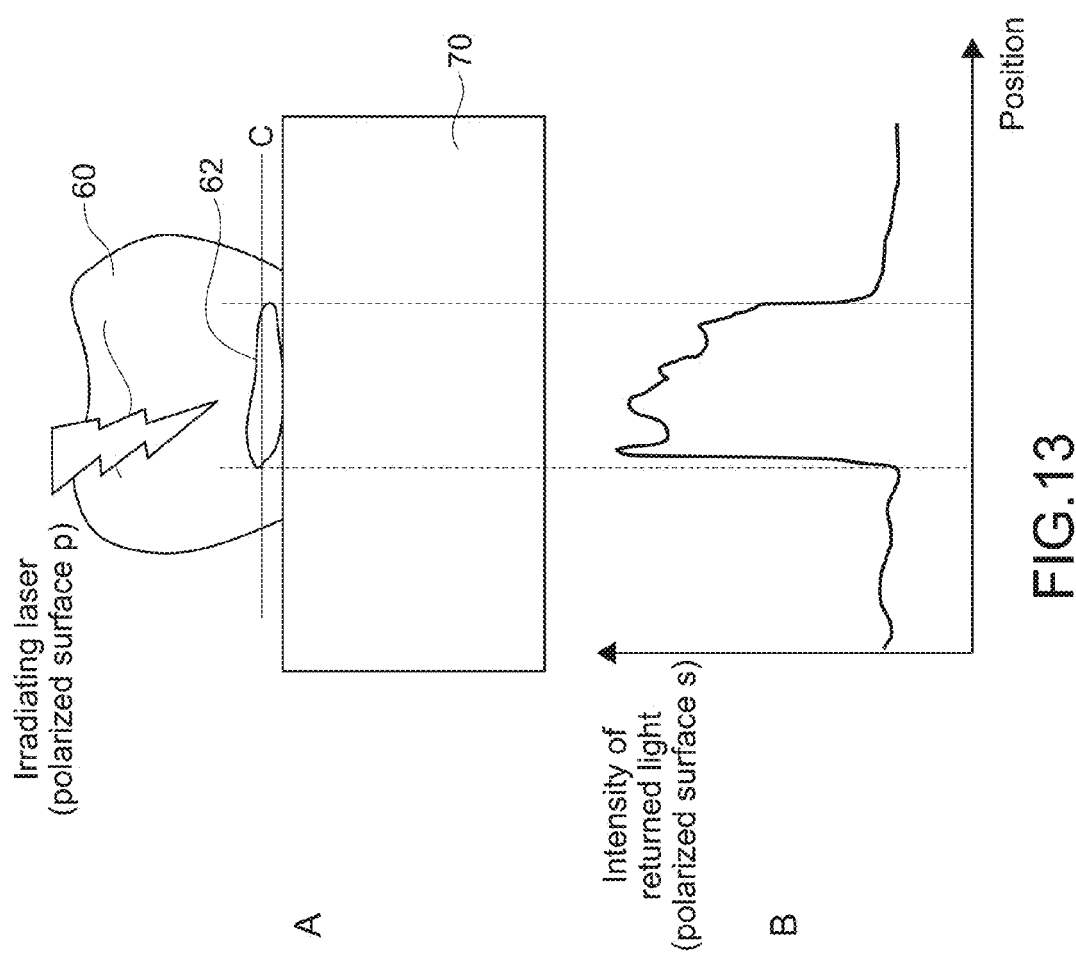
FIGS. 13A and 13B illustrate a method of discerning a plaque from a calculus according to a third embodiment.

FIGS. 13A and 13B illustrate a discerning method using the p-polarized light as the irradiation light. FIG. 13A shows a status that the oral cavity is irradiated with the p-polarized light. FIG. 13B is a graph of the intensity of the s-polarized light component of the returned light to the p-polarized light irradiation, when the oral cavity is scanned along a line C including a calculus site.

The calculi have rougher surfaces than the teeth. By evaluating a disturbance of the polarized light due to a surface roughness, the calculi and the teeth can be discerned. When the oral cavity is irradiated with the p-polarized light, the polarized surface is disturbed by the surface roughness of the calculi. Therefore, the intensity of the s-polarized light of the returned light on the calculi is greater than that on the teeth.

As shown in FIG. 13B, the s-polarized light intensity of the returned light at the calculus site 62 will be higher than that at the tooth 60.

In this way, with the s-polarized light intensity of the returned light, the calculi and the teeth can be discerned.

Also, as the irradiation light, the s-polarized light may be used instead of the p-polarized light. In this case, the p-polarized light component of the returned light is analyzed to discern the calculi and the teeth. A principle of discernment is similar to the irradiation light of the p-polarized light.

In the second embodiment, the p-polarized light irradiation is described as an example.

The control unit 122 discerns the plaque site, the calculus site, and a tooth site based on the reflected light intensity distribution by the irradiation of the near-infrared light, and the s-polarized light intensity of the returned light by the p-polarized light irradiation.

The control unit 122 correlates the image data to which the positional data is linked with the data of the reflected light and the data of the s-polarized light (data of the s-polarized light intensity of the returned light) to which the positional data is linked, and generates the data for highlighting and displaying the plaque site and the calculus site on the image of the oral cavity so that the plaque site and the calculus site can be discerned by coloring. As shown in FIG. 9 or FIG. 12, the control unit 122 displays the highlighted and displayed image of the plaque site 61 and calculus site 62 colored on the image of the oral cavity image-captured by the image capturing unit. In the highlighting and displaying, the plaque site and the calculus site may be colored in different colors and displayed, may have different color densities in similar colors and displayed or the like, so that the plaque site and the calculus site can be discerned.

Further, similar to the control unit 22 in the first embodiment, the control unit 122 generates the data for displaying the temporal change in the status of the plaque site 61 by the oral care based on the reflected light amount by the temporal change.

[Image Acquisition Method]

Next, the method of acquiring the image for highlighting and displaying the plaque site and the calculus site will be described using the above-described electrical toothbrush 101.

Figure 10:
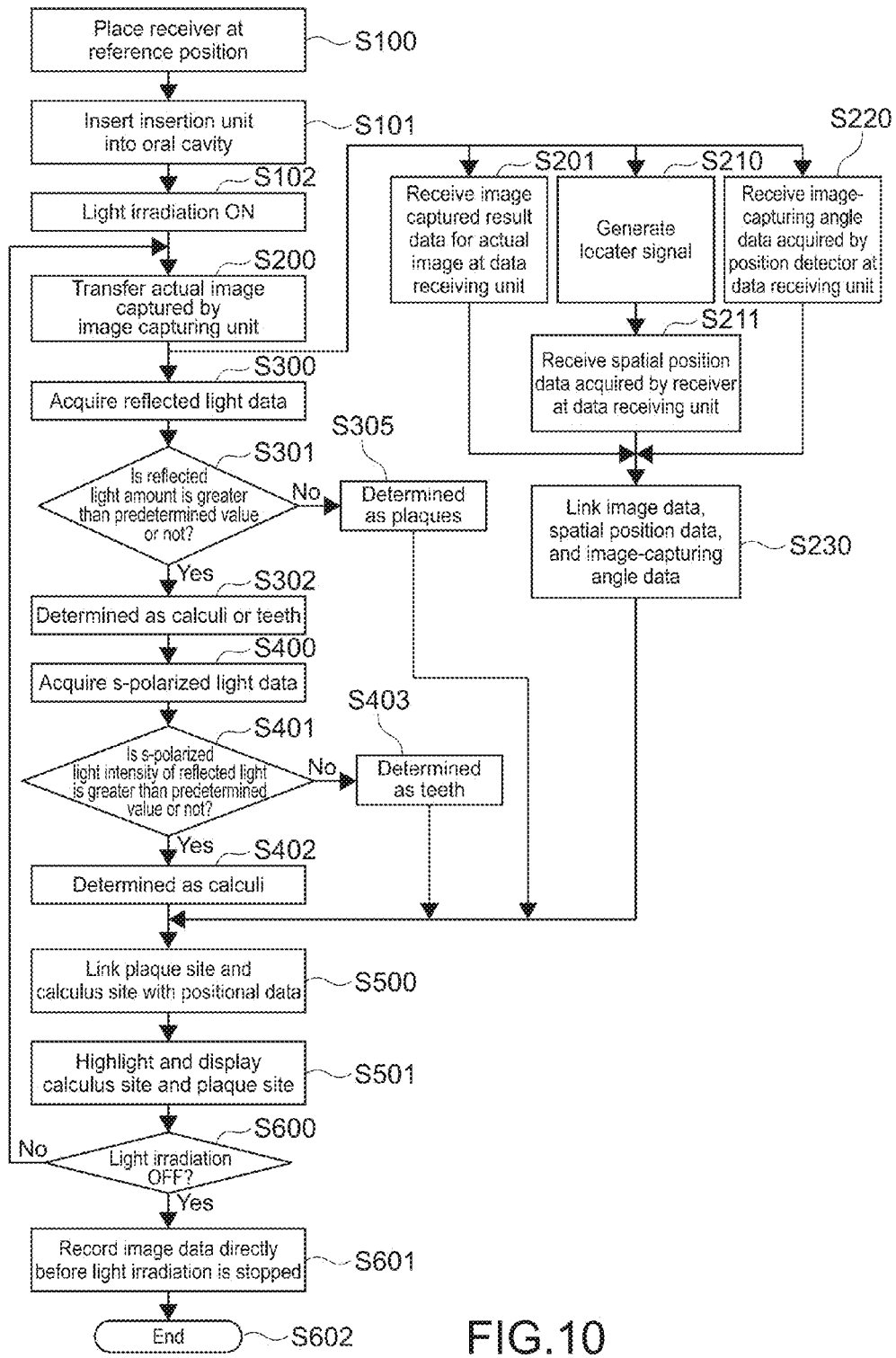
FIG. 10 is a flow diagram showing a flow of image acquisition using the dental apparatus shown in FIG. 9.

FIG. 10 is a flow diagram for acquiring the image for highlighting and displaying the plaque site and the calculus site according to the second embodiment. Hereinafter, it will be described along the flow shown in FIG. 10.

(Image Acquisition Preparation Processing, an S100 Number)

Firstly, as shown in FIG. 10, the user places the receiver 7 for the right ear lobe as the reference position (S100).

Next, the user inserts the insertion unit 110 emitting the locator signal of the electrical toothbrush 101 into the user's oral cavity (S101), and turns on the electrical toothbrush 101 to vibrate the brush 130. At the same time, the irradiation light including the image capturing light, the near-infrared light, and the p-polarized light are emitted from the light source 114. The light irradiation unit 112 emits the light (S102).

(Image Acquisition Processing in Oral Cavity, an S200 Number)

The image capturing unit 115 captures an image of the oral cavity to which the light is irradiated from the light irradiation unit 112, and acquires the data of the image captured result for the actual image in the oral cavity. The output unit 116 outputs the data of the image captured result for the actual image to the image processing unit 124 (S200).

The image processing unit 124 receives the data of the image captured result for the actual image (actual image data) transmitted from the output unit 116 (S201).

(Acquisition Processing of Spatial Position Data, an S210 Number)

The locater signal generation unit 19 of the electric toothbrush 101 generates a locater signal (S210).

The receiver 7 receives the locater signal, and transmits it as the data of the absolute spatial position to the data receiving unit 124. The data receiving unit 124 receives the data of the absolute spatial position (S211). The place where the receiver 7 is placed is set to the reference position. The data of the absolute spatial position is detected from the reference position.

(Acquisition Processing of Image-Capturing Angle Data, S220)

The position detector 18 of the electric toothbrush 101 detects a direction (the image-capturing angle) of the electric toothbrush 101. The image-capturing angle data detected is transmitted to the data receiving unit 124 by the output unit 116, and the data receiving unit 124 receives the image-capturing angle data (S220).

(Linking Processing of Image Data and Positional Data, S230)

The image processing unit 123 links the image captured result for the actual image acquired at S201, the data of the absolute spatial position acquired at S211, and the data of the image-capturing angle acquired at S220 (S230).

(Discerning Processing of Plaques, Calculi, and Teeth, an S300 Number)

The image processing unit 123 maps gradationally a reflected light intensity from the data of the image captured result for the actual image received by the data receiving unit 124, and acquires a reflected light intensity distribution (the data of the reflected light) (S300).

The control unit 122 determines whether or not the reflected light amount is greater than the predetermined value (S301).

When the control unit 122 determines that the reflected light amount is not greater at S301 (No), the site showing the reflected light amount is determined as the plaque site (S305).

When the control unit 122 determines that the reflected light amount is greater at S301 (Yes), the site showing the reflected light amount is determined as the plaque site or the tooth site (S302).

(Discerning Calculi from Teeth)

The image processing unit 123 acquires an s-polarized light intensity distribution (the data of the s-polarized light)) of the returned light received at the data receiving unit 124 (S400).

The control unit 122 compares the s-polarized light intensity of the returned light with a profile of the irradiation light, and determines whether or not the s-polarized light intensity is greater than the predetermined value (S401).

When the control unit 122 determines that the s-polarized light intensity is not greater at S401 (No), the site is determined as the tooth site (S403).

When the control unit 122 determines that the s-polarized light intensity is greater at S401 (Yes), the site is determined as the plaque site (S402).

(Image Acquisition Processing of Plaque Site and Calculus Site Highlighted and Displayed, an S500 Number)

The image processing unit 123 links the plaque site and the calculus site with the positional data (S500).

The control unit 122 correlates the image data to which the positional data is linked with the plaque site and the tooth site to each of which the positional data is linked, and generates the data for highlighting and displaying the plaque site and the calculus site on the image of the oral cavity. The control unit 122 displays the plaque site 61 and the calculus sites 62 highlighted and displayed of the image of the oral cavity image-captured by the image capturing unit on the display unit 201 as shown in FIG. 8 (S501).

(End Processing, an S600 Number)

Next, it is determined whether or not the light irradiation by the practitioner is turned off (S600).

At S600, when the control unit determines that the light irradiation is turned off (Yes), the control unit 122 records the image data directly before the light irradiation is stopped (S601), and ends the care (S602).

When the control unit determines that the light irradiation is not turned off at S600 (No), the flow is returned to S200, and the processing is repeated.

As described above, the plaques contain a higher water content than the teeth and the calculi. Therefore the reflected light amounts to the near-infrared rays of the plaques, the calculi, and the teeth are different, and the plaques, the calculi, and the teeth can be discerned. In addition, by analyzing the polarized light status of the returned light to the p-polarized light irradiation and comparing it with the profile of the irradiation light, the calculi and the teeth can be discerned. By acquiring the image for highlighting and displaying the plaque site and the calculus site being capable of discerning, the plaque site and the calculus site can be perceived by the user, and the oral care is effectively done.

In addition, the status of the plaque site can be viewed by the user, and the user may have a motive to visit a dental office. Furthermore, when a certain amount of the plaques is detected, the electric toothbrush 101 may have a function to generate a voice to encourage the user to visit a dental office for plaque removal.

Alternatively, the electric toothbrush 101 may have a configuration that the temporal change in the status of the plaque site by the oral care, as in the first embodiment.

Next, a third embodiment will be described.

Third Embodiment

Although in the second embodiment, the p-polarized light is used as the irradiation light, and the calculi and the teeth are discerned by the s-polarized intensity of the returned light, the calculi and the teeth may be discerned by the scattering degree of the reflected light.

The third embodiment is described below referring to FIGS. 14A, 14C and 14D.

Figure 14:
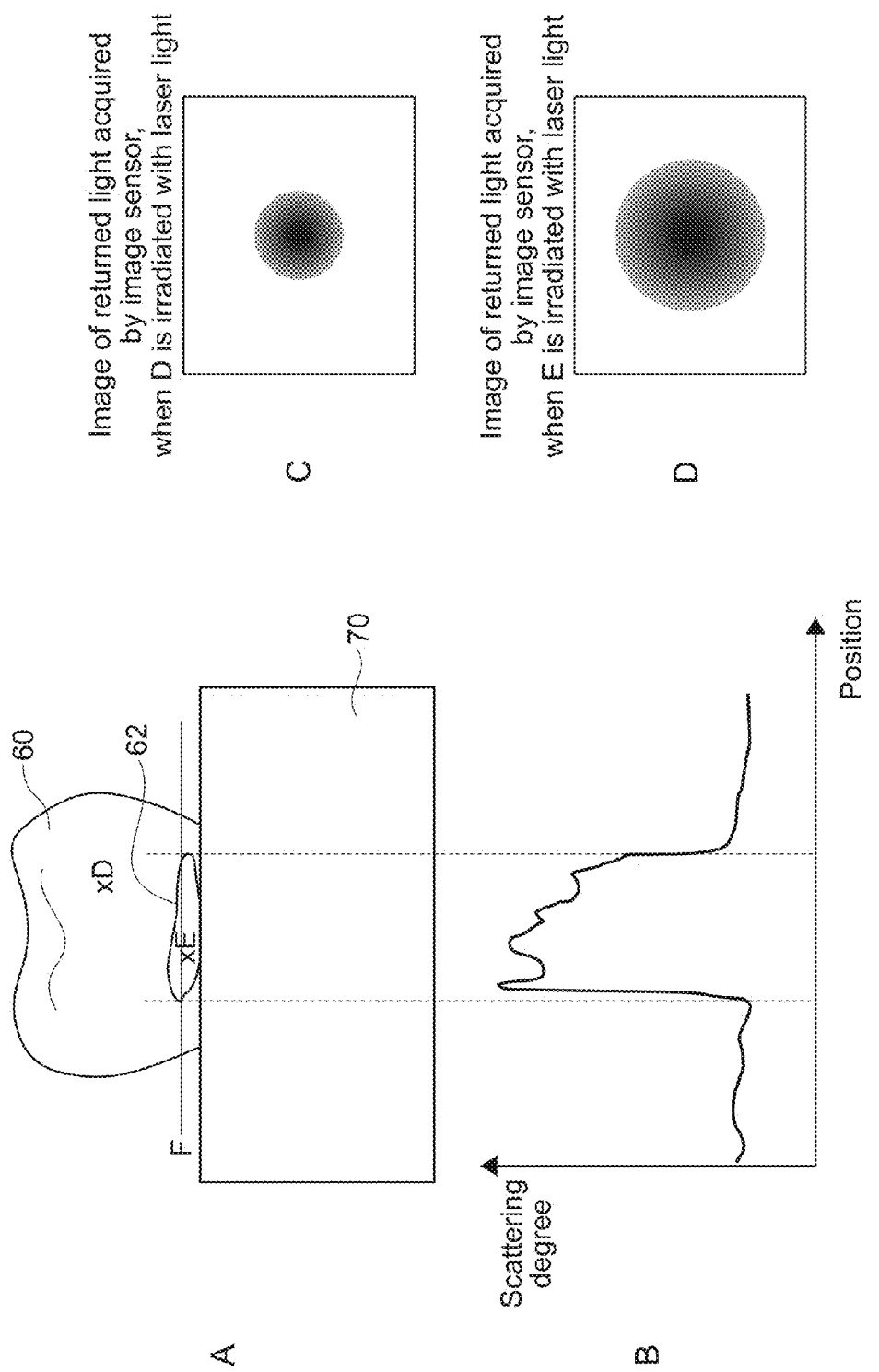
FIGS. 14A to 14D are diagrams for illustrating another method of discerning a plaque from a calculus according to a fourth embodiment.

FIGS. 14A to 14D are diagrams for illustrating a discerning method using a laser light as the irradiation light. FIG. 14C is an image of a returned light acquired by an image sensor, when a tooth 60 shown in FIG. 14A is irradiated with a laser light at a position D. FIG. 14D is an image of a returned light acquired by an image sensor, when a plaque site 62 shown in FIG. 14A is irradiated with a laser light at a position E.

In the discerning method according to the third embodiment, the oral cavity is firstly irradiated with the laser light.

The calculi have rougher surfaces than the teeth. By evaluating the scattering degree due to a surface roughness, the calculi and the teeth can be discerned. The light irradiated to the teeth not roughened is less scattered and is reflected and returned. In contrast, the light irradiated to the calculi roughened is scattered and returned.

The laser light incident on the position D that is the tooth is less scattered and is reflected and returned. In contrast, the light incident on the position E that is the calculus site is scattered and returned by the surface roughness of the calculus. As shown in FIGS. 14C and 14D, by comparing intensity profiles of the returned light from the both, the profile of the returned light from the tooth shows a sharper and smaller distribution than that of the profile of the returned light from the calculus.

In this way, the profile of the returned light can specify the calculus site.

Alternatively, the laser light may be used as the irradiation light and the light intensity of the returned light may be used as an indicator of the scattering degree to discern the calculus from the teeth.

FIG. 14B is a graph of the scattering degree when the oral cavity is scanned along a line F including a calculus site shown in FIG. 14A.

As shown in FIG. 14B, the scattering degree of the reflected light in the calculus site 62 has higher than in the tooth 60.

Thus, the calculi and the teeth can be discerned by the scattering degree of the reflected light.

Next, a fourth embodiment will be described.

Fourth Embodiment

In the second embodiment, the oral cavity is irradiated with the near-infrared rays, and the plaques and the teeth are discerned based on the reflected light amount. However, the plaque staining agent may be administered to the oral cavity, the oral cavity stained by the plaque staining agent may be image-captured by the image capturing unit, and the plaque site may be highlighted and displayed on the image of the oral cavity based on the image captured result.

Figure 15:
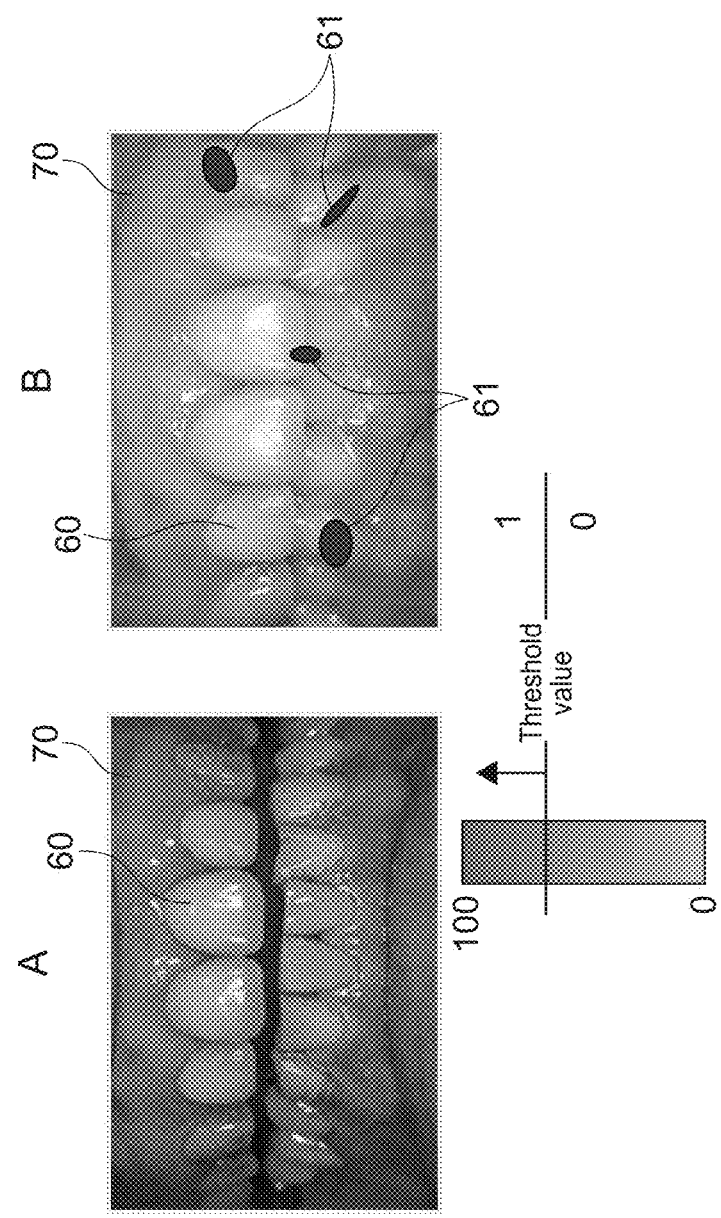
FIGS. 15A and 15B are diagrams for illustrating a method of discerning a plaque site using a plaque staining agent according to a fifth embodiment.

FIG. 15A shows an image acquired by staining the oral cavity with the plaque staining agent. FIG. 15B shows an image where the plaque site is discerned by another method in the third embodiment, and the plaque sites are highlighted and displayed.

In the discerning method according to the third embodiment, the plaque staining agent is administered to the oral cavity to stain the oral cavity with the plaque staining agent. Then, the oral cavity stained is image-captured by the image capturing unit.

A density stained by the plaque staining agent is expressed in stepwise, for example, gradient from 0 to 100. A threshold value is defined to binarize the density. For example, when the threshold value is defined to be 70, the degree of staining is binarized such that the value of 70 to 100 is defined as "1", and the value smaller than 70 is defined as "0". A site determined as "1" denotes the plaque site, and a site determined as "0" denotes the teeth.

As shown in FIG. 15B, in the image of the oral cavity acquired by the image capturing unit, the sites determined as "1", i.e., the sites determined as the plaque site are colored, highlighted and displayed.

In this way, the plaque sites can be discerned by the degree of staining by the plaque staining agent, highlighted and displayed.

Next, a fifth embodiment will be described.

Fifth Embodiment

Other than the methods of discerning the plaque site as described above, a blue light is used as the irradiation light, the light from the oral cavity emitted to the blue light irradiated is image-captured by the image capturing unit. From the image captured result, the plaque site can be discerned.

The plaque emits fluorescence (autofluorescence) by irradiating with the blue light. Utilizing this, the plaque site can be discerned.

The present technology may have the following configurations.

(1) A dental apparatus, including:
a light irradiation unit for emitting a light to irradiate an oral cavity;
an image capturing unit for image-capturing the oral cavity light irradiated by the light irradiation unit; and
an output unit for outputting data for highlighting and displaying a plaque site or a calculus site on an image of the oral cavity based on an image captured result by the image capturing unit.

(2) The dental apparatus according to (1) above, in which
a light source emits a near-infrared light, and
the output unit outputs the data for highlighting and displaying the plaque site or the calculus site on the image of the oral cavity based on a reflected light amount from the oral cavity emitted to the near-infrared rays irradiated by the light irradiation unit.

(3) The dental apparatus according to (2) above, in which
the output unit outputs the data for highlighting and displaying being capable of discerning the plaque site and the calculus site on the image of the oral cavity based on the reflected light amount from the oral cavity emitted to the near-infrared rays irradiated by the light irradiation unit.

(4) The dental apparatus according to (1) or (2) above, in which
the light irradiation unit emits p-polarized light, and
the output unit outputs the data for highlighting and displaying the calculus site on the image of the oral cavity based on an s-polarized light amount of a returned light from the oral cavity emitted to the p-polarized light irradiated by the light irradiation unit.

(5) The dental apparatus according to (1) or (2) above, in which
the light irradiation unit emits s-polarized light, and
the output unit outputs the data for highlighting and displaying the calculus site on the image of the oral cavity based on an p-polarized light amount of a returned light from the oral cavity emitted to the s-polarized light irradiated by the light irradiation unit.

(6) The dental apparatus according to (1) or (2) above, in which
the output unit outputs the data for highlighting and displaying the calculus site on the image of the oral cavity based on a scattering degree of a reflected light from the oral cavity emitted to the light irradiated by the light irradiation unit.

(7) The dental apparatus according to (1) above, in which
the light irradiation unit emits a blue light, and
the output unit outputs the data for highlighting and displaying the plaque site on the image of the oral cavity based on a light amount from the oral cavity emitted to the blue light irradiated by the light irradiation unit.

(8) The dental apparatus according to (1) above, in which
a plaque staining agent is administered to the oral cavity, and
the output unit outputs the data for highlighting and displaying the plaque site on the image of the oral cavity based on a color density stained by the plaque staining agent.

(9) The dental apparatus according to any one of (1) to (8) above, in which
the output unit outputs the data for visualizing a status change of the plaque site or the calculus site in the oral cavity.

(10) The dental apparatus according to any one of (1) to (9) above, in which
the output unit outputs the data for being audible of a status change of the plaque site or the calculus site in the oral cavity.

(11) A dental apparatus, including:
an insertion unit that is inserted into an oral cavity;
a gripper unit that is connected to the insertion unit;
a light irradiation unit, disposed on the insertion unit, for emitting a light for irradiating the oral cavity; and
an image capturing unit, disposed on the insertion unit, for acquiring an image captured result of the oral cavity in order to output data for highlighting and displaying the plaque site or the calculus site on the image of the oral cavity.

(12) The dental apparatus according to (11) above, further including a cleaning unit for cleaning the oral cavity.

(13) The dental apparatus according to (11) or (12) above,
the light irradiation unit emits near-infrared rays, and
the data is for highlighting and displaying the plaque site or the calculus site on the image of the oral cavity based on a reflected light amount from the oral cavity emitted to the near-infrared rays irradiated by the light irradiation unit.

(14) The dental apparatus according to (13) above,
the data is for highlighting and displaying the plaque site and the calculus site being capable of discerning on the image of the oral cavity based on a reflected light amount from the oral cavity emitted to the near-infrared rays irradiated by the light irradiation unit.

(15) The dental apparatus according to any one of (11) to (13) above, in which
the light irradiation unit emits p-polarized light, and
the data is for highlighting and displaying the calculus site on the image of the oral cavity based on an s-polarized light amount of a returned light from the oral cavity emitted to the p-polarized light irradiated by the light irradiation unit.

(16) The dental apparatus according to any one of (11) to (13) above, in which
the light irradiation unit emits s-polarized light, and
the data is for highlighting and displaying the calculus site on the image of the oral cavity based on a p-polarized light amount of a returned light from the oral cavity emitted to the s-polarized light irradiated by the light irradiation unit.

(17) The dental apparatus according to any one of (11) to (13) above, in which
the data is for highlighting and displaying the plaque site and the calculus site being capable of discerning on the image of the oral cavity based on a scattering degree of the returned light from the oral cavity emitted to the light irradiated by the light irradiation unit.

(18) The dental apparatus according to (11) or (12) above, in which
the light irradiation unit emits a blue light, and
the data is for highlighting and displaying the plaque site on the image of the oral cavity based on a light amount from the oral cavity emitted to the blue light irradiated by the light irradiation unit.

(19) The dental apparatus according to (11) or (12) above, in which
a plaque staining agent is administered to the oral cavity, and
the data is for highlighting and displaying the plaque site on the image of the oral cavity based on a color density stained by the plaque staining agent.

(20) The dental apparatus according to any one of (11) to (19) above, in which
the image capturing unit acquires the data for visualizing a status change of the plaque site or the calculus site in the oral cavity.

(21) The dental apparatus according to any one of (11) to (20) above, in which
the image capturing unit acquires the data for being audible of a status change of the plaque site or the calculus site in the oral cavity.

(22) A method of acquiring an image, including:
image-capturing an oral cavity to acquire an image of the oral cavity;
irradiating the oral cavity with a light;
image-capturing the oral cavity light irradiated; and
generating data for highlighting and displaying a plaque site or a calculus site on the image of the oral cavity based on an image captured result by an image capturing unit.

(23) The method of acquiring an image according to (22) above, in which
the light is near-infrared rays, and
the data is for highlighting and displaying the plaque site or the calculus site on the image of the oral cavity based on a reflected light amount from the oral cavity emitted to the near-infrared rays irradiated by the light irradiation unit.

(24) The method of acquiring an image according to (23) above, in which
the data is for highlighting and displaying the plaque site and the calculus site being capable of discerning on the image of the oral cavity based on the reflected light amount from the oral cavity emitted to the near-infrared rays irradiated by the light irradiation unit.

(25) The method of acquiring an image according to (22) or (23) above, in which
the light is p-polarized light, and
the data is for highlighting and displaying the calculus site on the image of the oral cavity based on an s-polarized light amount of a returned light from the oral cavity emitted to the p-polarized light irradiated by the light irradiation unit.

(26) The method of acquiring an image according to (22) or (23) above, in which
the light is s-polarized light, and
the data is for highlighting and displaying the calculus site on the image of the oral cavity based on a p-polarized light amount of the returned light from the oral cavity emitted to the s-polarized light irradiated by the light irradiation unit.

(27) The method of acquiring an image according to (22) or (23) above, in which
the data is for highlighting and displaying the calculus site on the image of the oral cavity based on a scattering degree of the returned light from the oral cavity emitted to the light irradiated by the light irradiation unit.

(28) The method of acquiring an image according to (22) above, in which
the light is a blue light, and
the data is for highlighting and displaying the plaque site on the image of the oral cavity based on a light amount from the oral cavity emitted to the blue light irradiated by the light irradiation unit.

(29) The method of acquiring an image according to (22) above, in which
the oral cavity is stained with a plaque staining agent, and
the data is for highlighting and displaying the plaque site on the image of the oral cavity based on a color density stained by the plaque staining agent.

(30) The method of acquiring an image according to any of (22) to (29) above, in which
based on the image captured result, the data for visualizing a status change of the plaque site or the calculus site in the oral cavity is generated.

(31) The method of acquiring an image according to any of (22) to (30) above, in which
based on the image captured result, the data for being audible of a status change of the plaque site or the calculus site in the oral cavity is generated.

(32) An image processing unit, including:
a receiving unit for receiving an image captured result of an oral cavity;
a control unit for generating an image for highlighting and displaying the plaque site or the calculus site on an image of the oral cavity based on the image captured result.

The present technology contains subject matter related to that disclosed in Japanese Priority Patent Application JP 2012-125760 filed in the Japan Patent Office on Jun. 1, 2012, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A dental apparatus, comprising:
a light irradiation unit for emitting a near-infrared light to irradiate an oral cavity;
an image capturing unit for image-capturing the oral cavity light irradiated by the light irradiation unit; and
an output unit programmed to output data for highlighting and displaying that discerns between a plaque site and a calculus site on an image of the oral cavity based on a reflected light amount from an image captured result by the image capturing unit.

2. The dental apparatus according to claim 1, wherein
the light irradiation unit further emits p-polarized light, and at least a portion of the data for highlighting and displaying the calculus site on the image of the oral cavity is based on an s-polarized light amount of a returned light from the oral cavity.

3. The dental apparatus according to claim 1, wherein
the light irradiation unit further emits s-polarized light, and
at least a portion of the data for highlighting and displaying the calculus site on the image of the oral cavity is based on a p-polarized light amount of a returned light from the oral cavity.

4. The dental apparatus according to claim 1, wherein
at least a portion of the data for highlighting and displaying the calculus site on the image of the oral cavity is based on a scattering degree of a returned light from the oral cavity.

5. The dental apparatus according to claim 1, wherein
the light irradiation unit further emits a blue light, and
at least a portion of the data for highlighting and displaying the plaque site on the image of the oral cavity is based on a light amount from the oral cavity emitted from the blue light.

6. The dental apparatus according to claim 1, wherein
a plaque staining agent is administered to the oral cavity, and
at least a portion of the data for highlighting and displaying the plaque site on the image of the oral cavity is based on a color density stained by the plaque staining agent.

7. The dental apparatus according to claim 1, wherein the output unit outputs the data for visualizing a status change of at least one of the plaque site and the calculus site in the oral cavity.

8. The dental apparatus according to claim 1, wherein
the output unit outputs the data for being audible of a status change of at least one of the plaque site and the calculus site in the oral cavity.

9. A dental apparatus, comprising:
an insertion unit that is inserted into an oral cavity;
a gripper unit that is connected to the insertion unit;
a light irradiation unit, disposed on the insertion unit, for emitting a near-infrared light for irradiating the oral cavity; and
an image capturing unit, disposed on the insertion unit, that acquires an image captured result of the oral cavity and generates data for highlighting and displaying that discerns between a plaque site and a calculus site on an image of the oral cavity based on a reflected light amount from the image captured result.

10. The dental apparatus according to claim 9, further including a cleaning unit for cleaning the oral cavity.

11. An image processing unit, comprising:
a receiving unit for receiving an image captured result of an oral cavity;
a control unit that generates an image for highlighting and displaying that discerns between a plaque site and a calculus site on an image of the oral cavity based on a reflected light amount from the image captured result; and
a display unit for displaying the image generated.

12. A method of acquiring an image, comprising:
irradiating an oral cavity with a near-infrared light;
image-capturing the oral cavity light irradiated; and
generating data for highlighting and displaying that discerns between a plaque site and a calculus site on an image of the oral cavity based on a reflected light amount from an image captured result.

* * * * *